(12) United States Patent
Yoo

(10) Patent No.: US 11,717,216 B2
(45) Date of Patent: Aug. 8, 2023

(54) WEARABLE BODY FAT COMBUSTION MEASUREMENT DEVICE

(71) Applicant: SENTECH KOREA CORP., Paju-si (KR)

(72) Inventor: Do Joon Yoo, Seongnam-si (KR)

(73) Assignee: SENTECH KOREA CORP., Paju-si (KR)

( * ) Notice: Subject to any disclaimer, the term of this patent is extended or adjusted under 35 U.S.C. 154(b) by 665 days.

(21) Appl. No.: 16/611,587

(22) PCT Filed: May 4, 2018

(86) PCT No.: PCT/KR2018/005186
§ 371 (c)(1),
(2) Date: Nov. 7, 2019

(87) PCT Pub. No.: WO2018/208050
PCT Pub. Date: Nov. 15, 2018

(65) Prior Publication Data
US 2020/0155064 A1 May 21, 2020

(30) Foreign Application Priority Data
May 8, 2017 (KR) .................. 10-2017-0057142

(51) Int. Cl.
*A61B 5/00* (2006.01)
*A61B 5/145* (2006.01)

(52) U.S. Cl.
CPC ........ *A61B 5/4872* (2013.01); *A61B 5/14517* (2013.01); *A61B 5/7271* (2013.01);
(Continued)

(58) Field of Classification Search
CPC . A61B 5/4872; A61B 5/14517; A61B 5/7271; A61B 5/6831; A61B 2562/0271; A61B 2562/029
See application file for complete search history.

(56) References Cited

U.S. PATENT DOCUMENTS 10,410,538 B2 * 9/2019 Simpson ................ G16H 50/20
2003/0208133 A1 * 11/2003 Mault .................... A61B 5/087
600/531

(Continued)

FOREIGN PATENT DOCUMENTS

JP 4005029 B2 11/2007
JP 2010281698 A * 12/2010
(Continued)

*Primary Examiner* — Puya Agahi
*Assistant Examiner* — Grace L Rozanski
(74) *Attorney, Agent, or Firm* — NKL Law; Jae Youn Kim

(57) ABSTRACT

A wearable body fat combustion measurement device includes a housing including a first chamber with an opening, a fixing means attached to the housing and configured to bring the housing into close contact with a user's skin in a state in which the opening of the first chamber faces the user's skin, a measurement sensor disposed inside the first chamber and configured to generate an electrical signal according to an amount of acetone contained in a gas evaporated from sweat discharged from the user's skin and introduced into the first chamber through the opening, a reference sensor disposed outside the first chamber and configured to generate an electrical signal according to a concentration of a gas component contained in an ambient air and detectable by the measurement sensor, and a signal processor configured to process the electrical signals received from the measurement sensor and the reference sensor.

7 Claims, 3 Drawing Sheets

(52) U.S. Cl.
CPC ....... *A61B 5/6831* (2013.01); *A61B 2562/029* (2013.01); *A61B 2562/0271* (2013.01)

(56) References Cited

U.S. PATENT DOCUMENTS

| | | | | |
|---|---|---|---|---|
| 2010/0310425 A1* | 12/2010 | Piper | ................... | A61B 5/0059 |
| | | | | 422/86 |
| 2011/0034792 A1* | 2/2011 | Williams | ........... | A61B 5/14532 |
| | | | | 600/365 |
| 2016/0270704 A1* | 9/2016 | DeTurk | ................ | A61B 5/4872 |
| 2018/0317844 A1* | 11/2018 | Deturk | ................. | A61B 5/0261 |
| 2019/0223789 A1* | 7/2019 | Wang | ................. | G01R 33/5602 |

FOREIGN PATENT DOCUMENTS

| | | | |
|---|---|---|---|
| JP | 2014-010046 A | | 1/2014 |
| JP | 2014-157125 A | | 8/2014 |
| JP | 2015-167575 A | | 9/2015 |
| JP | 2017083337 A | * | 5/2017 |
| KR | 10-2015-0061231 A | | 6/2015 |
| KR | 10-2016-0024412 A | | 3/2016 |
| KR | 10-2016-0107752 A | | 9/2016 |
| KR | 10-1691142 B1 | | 1/2017 |

* cited by examiner

WEARABLE BODY FAT COMBUSTION MEASUREMENT DEVICE

TECHNICAL FIELD

The present invention relates to a wearable body fat combustion measurement device, and more particularly, to a wearable body fat combustion measurement device capable of measuring the combustion amount of body fat by detecting acetone evaporated from a user's sweat. This work was supported by the Technology Innovation Program (or Industrial Strategic Technology Development Program-Advanced Technology Center Association (ATC)) (10076984, Development of ROIC Embedded Semiconducting MEMS gas sensor and Smart wearable Devices for Transdermal Analyte Concentration (TAC)) funded By the Ministry of Trade, Industry & Energy (MOTIE, Korea).

BACKGROUND ART

The source of energy used by a human body is mainly blood sugar referred to as glucose, protein or body fat. It is known that the human body primarily uses blood sugar as an energy source, then protein and finally fat. Therefore, blood sugar is usually used as a main energy source. However, body fat is used as an energy source in special situations such as diabetes, starvation due to fasting, energy consumption due to intense exercise, dietary progression through carbohydrate intake restriction, and the like.

When the human body uses body fat as an energy source, ketone bodies are produced as a product of lipolysis. The ketone bodies are a generic term for three substances, including acetoacetic acid, β-hydroxybutyric acid and acetone produced by decarbonation of these substances. The ketone bodies are produced in the liver of the human body and circulated together with the blood. It is known that a part of the ketone bodies is used as an energy source in the brain and the rest thereof is discharged as an exhaled gas through the lungs and excreted as urine. If it is possible to detect a trace amount of ketone bodies existing in the blood, it is possible to see how much body fat is combusting. Therefore, the detection of the ketone bodies in the blood can be very useful for diet programs aimed at reducing body fat.

A urine test and a blood test are the most common methods to determine a concentration of ketone bodies in the human body.

The urine test is a method of determining a concentration of ketone bodies in the human body based on a change in the color of a test paper according to the concentration of ketone bodies contained in the urine. The urine test has an advantage in that it is a relatively simple measurement method. However, the urine test is not suitable as a quantitative analysis method because the test results vary greatly depending on the water intake or the like. In addition, there is a problem that it is difficult to continuously measure a body fat combustion amount.

The blood test can measure quantitatively the amount of ketone bodies present in the blood in a relatively accurate manner. However, it is cumbersome to collect the blood.

In addition to the ketone body concentration measurement method described above, a technique for measuring an amount of ketone bodies in the blood by analyzing an exhaled gas has been studied in recent years. Acetone contained in the exhaled gas is closely related to the amount of ketone bodies contained in the blood. Therefore, the amount of ketone bodies in the blood can be calculated by measuring the amount of acetone contained in the exhaled gas. The exhaled gas mainly contains acetone in the ketone bodies.

The method of analyzing the exhaled gas is very convenient as compared to other methods. However, it is somewhat inconvenient in that the exhaled gas has to be blown every time.

PRIOR ART DOCUMENTS

Patent Document 1: Korean Patent Application Publication No. 10-2015-0061231
Patent Document 2: Korean Patent Application Publication No. 10-2016-0024412
Patent Document 3: Korean Patent No. 10-1691142

SUMMARY

With the aforementioned problems in view, it is an object of the present invention to provide a wearable body fat combustion measurement device that can continuously measure a body fat combustion amount by measuring an amount of acetone contained in sweat through the use of a gas sensor.

According to one aspect of the present invention, there is provided a wearable body fat combustion measurement device, comprising: a housing including a first chamber with an opening; a fixing means attached to the housing and configured to bring the housing into close contact with a user's skin in a state in which the opening of the first chamber faces the user's skin; a measurement sensor disposed inside the first chamber and configured to generate an electrical signal according to an amount of acetone contained in a gas evaporated from sweat discharged from the user's skin and introduced into the first chamber through the opening; a reference sensor disposed outside the first chamber and configured to generate an electrical signal according to a concentration of a gas component contained in an ambient air and detectable by the measurement sensor; and a signal processor configured to process the electrical signals received from the measurement sensor and the reference sensor. The signal processor calculates a concentration of acetone by using the electrical signal received from the measurement sensor, calculates a concentration of a gas component contained in an ambient air and detectable by the measurement sensor by receiving the electrical signal from the reference sensor, and ignores the electrical signal received from the measurement sensor if the concentration of the gas component exceeds a predetermined value.

In the device, the measurement sensor and the reference sensor are of the same type.

In the device, the housing further includes a second chamber separated from the first chamber and configured introduce the ambient air, and the device further comprises: a printed circuit board configured to seal the first chamber with respect to the second chamber, the measurement sensor provided on one surface of the printed circuit board facing the first chamber, the reference sensor provided on the other surface of the printed circuit board facing the second chamber.

The device further comprises: a guide passage formed to surround the measurement sensor and configured to connect a surface of the printed circuit board on which the measurement sensor is provided and a surface of the housing on which the opening of the housing is formed, so as to guide the gas passing through the opening to the measurement sensor.

The device further comprises: a close contact member protruding toward the user's skin from a bottom surface of the housing facing the user's skin, the close contact member configured to surround the opening.

The device further comprises: a humidity sensor disposed inside the first chamber and configured to generate an electrical signal according to a humidity in the first chamber.

The device further comprises: a temperature sensor disposed inside the first chamber and configured to generate an electrical signal according to a temperature in the first chamber.

According to another aspect of the present invention, there is provided a wearable body fat combustion measurement device, comprising: a housing including a first chamber with an opening; a fixing means attached to the housing and configured to bring the housing into close contact with a user's skin in a state in which the opening of the first chamber faces the user's skin; a measurement sensor disposed inside the first chamber and configured to generate an electrical signal according to an amount of acetone contained in a gas evaporated from sweat discharged from the user's skin and introduced into the first chamber through the opening; a humidity sensor disposed inside the first chamber and configured to generate an electrical signal according to a humidity in the first chamber; and a signal processor configured to process the electrical signals received from the measurement sensor and the humidity sensor, wherein the signal processor calculates a concentration of acetone by using the electrical signal received from the measurement sensor, calculates a humidity in the first chamber by receiving the electrical signal from the humidity sensor, and ignores the electrical signal received from the measurement sensor if the humidity is less than a predetermined value.

According to a further aspect of the present invention, there is provided a wearable body fat combustion measurement device, comprising: a housing including a first chamber with an opening; a fixing means attached to the housing and configured to bring the housing into close contact with a user's skin in a state in which the opening of the first chamber faces the user's skin; a measurement sensor disposed inside the first chamber and configured to generate an electrical signal according to an amount of acetone contained in a gas evaporated from sweat discharged from the user's skin and introduced into the first chamber through the opening; a temperature sensor disposed inside the first chamber and configured to generate an electrical signal according to a temperature in the first chamber; and a signal processor configured to process the electrical signals received from the measurement sensor and the temperature sensor, wherein the signal processor calculates a concentration of acetone by using the electrical signal received from the measurement sensor, calculates a temperature in the first chamber by receiving the electrical signal from the temperature sensor, and ignores the electrical signal received from the measurement sensor if the temperature is less than a predetermined value.

The wearable body fat combustion measurement device according to the present disclosure has an advantage that it can continuously monitor a body fat combustion amount. In addition, there is an advantage that the body fat combustion amount can be measured by a simple method of wearing the device on the wrist, ankle, or the like.

DETAILED DESCRIPTION

Figure 1:
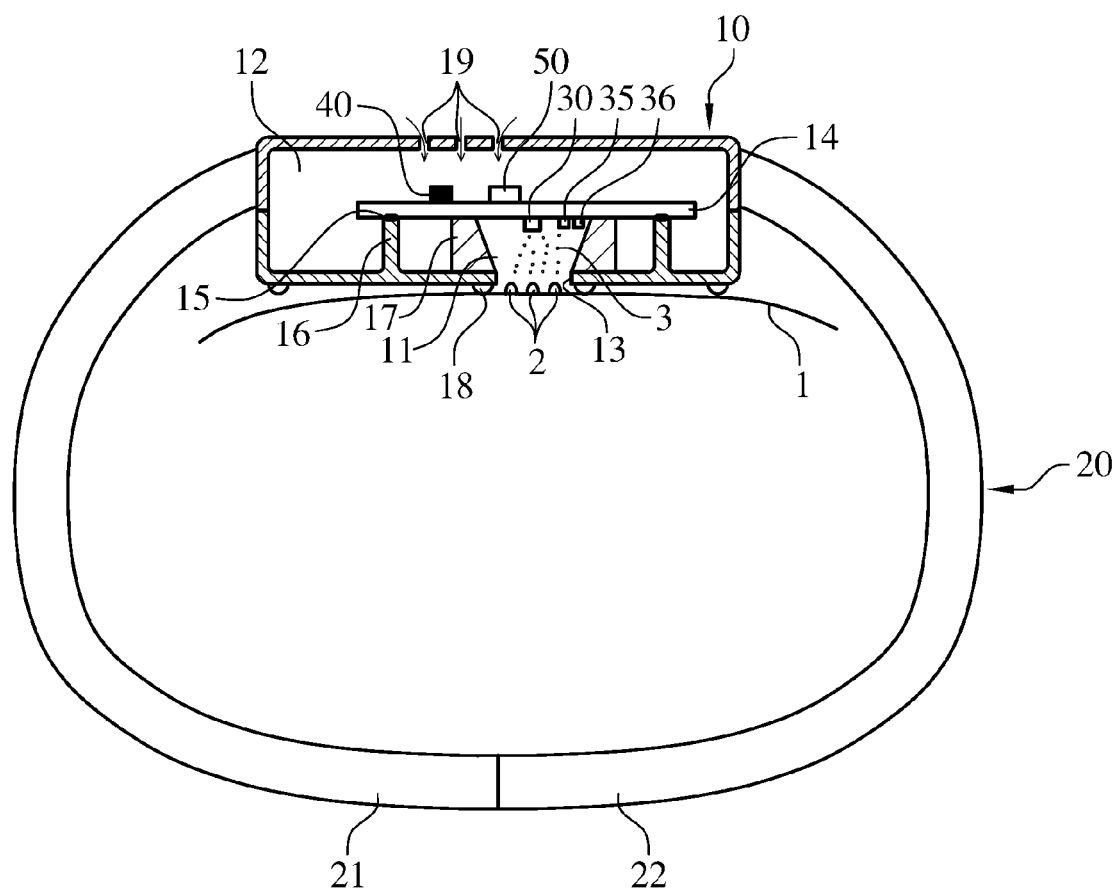
FIG. 1 is a configuration diagram of a wearable body fat combustion measurement device according to an embodiment of the present invention.

Hereinafter, a preferred embodiment of the present invention will be described in detail with reference to the accompanying drawings. The following embodiment is provided as an example to ensure that the spirit of the present invention is sufficiently conveyed to those skilled in the art. Therefore, the present invention is not limited to the embodiment described below and may be embodied in other forms. In the drawings, the width, length, thickness and the like of components may be exaggerated for the sake of convenience. The same components are denoted by like reference numerals throughout the specification.

FIG. 1 is a configuration diagram of a wearable body fat combustion measurement device according to an embodiment of the present invention. FIG. 1 illustrates a wearable body fat combustion measurement device 100 that may be attached to a wrist of a user using a band just like a wrist watch. FIG. 1 is illustrative. The wearable body fat combustion measurement device 100 may have a variety of forms such as an armband form, a form worn on an ankle using a band, and the like.

Referring to FIG. 1, the wearable body fat combustion measurement device 100 includes a housing 10, a fixing means 20, a measurement sensor 30 and a reference sensor 40.

The housing 10 may be made of plastic, metal, wood or a combination of these materials. A first chamber 11 and a second chamber 12 are formed in the housing 10.

The first chamber 11 is formed in a lower portion of the housing 10. An opening 13 is formed at the center of the bottom surface of the first chamber 11. When the user wears the wearable body fat combustion measurement device 100, the housing 10 is brought into close contact with the user's skin 1 with the opening 13 of the first chamber 11 facing the user's skin 1. Therefore, a gas 3 generated by the evaporation of sweat 2 discharged from the user's skin 1 is introduced into the first chamber 11.

The second chamber 12 is formed in an upper portion of the housing 10. The second chamber 12 has at least one through hole 19 or a through slit through which an ambient air can be introduced. The through hole 19 is preferably formed on the upper surface of the housing 10. This is because, if the through hole 19 is formed on the lower surface of the housing 10, the gas generated by the sweat 2 discharged from the user's skin 1 may also flow into the second chamber 12. In addition, the second chamber 12 is sealed with respect to the first chamber 11 in order to prevent the gas generated by the evaporation of the user's sweat 2 and introduced into the first chamber 11 from flowing into the second chamber 12. In the present embodiment, the second chamber 12 and the first chamber 11 are separated by a printed circuit board 14. The printed circuit board 14 may be coupled to the upper end of the side wall 16 of the first chamber 11 protruding from the bottom surface of the housing 10 through a sealing member 15 made of silicon or the like. The first chamber 11 and the second chamber 12 may be separated by a separate wall instead of the printed circuit board 14.

The fixing means 20 serves to bring the housing 10 into close contact with the skin 1 of the wrist of the user with the opening 13 of the first chamber 11 facing the user's skin 1. The fixing means 20 includes a first band strap 21 and a second band strap 22. The first band strap 21 and the second band strap 22 are respectively coupled to both sides of the housing 10. The fixing means 20 may be made integral with the housing 10. The first band strap 21 and the second band strap 22 may be made of leather, fabric, rubber, metal, or the like. The first band strap 21 and the second band strap 22 are coupled to each other to form a loop to tighten the wrist so that the housing 10 can be brought into close contact with the wrist. The first band strap 21 and the second band strap 22 may be coupled to each other through various well-known coupling means.

The measurement sensor 30 is arranged inside the first chamber 11. The measurement sensor 30 generates an electric signal according to the amount of acetone contained in the gas 3 generated by the evaporation of the sweat 2 discharged from the user's skin 1. As the measurement sensor 30, for example, a semiconductor gas sensor may be used. The measurement sensor 30 is provided on the lower surface of the printed circuit board 14 so as to face the opening 13.

The reference sensor 40 is disposed inside the second chamber 12. The reference sensor 40 generates an electrical signal according to the concentration of a component which is contained in the ambient air and detectable by the measurement sensor 30. The reference sensor 40 is preferably the same gas sensor as the measurement sensor 30.

Since the gas sensor does not have high selectivity, the measurement sensor 30 inevitably also generates an electrical signal according to a component other than acetone. For example, the semiconductor gas sensor generates an electrical signal in response to not only acetone but also volatile organic compounds (VOCs) such as benzene and acetylene, and ethanol. Since the first chamber 11 is not completely sealed with respect to the ambient air, the ambient air may also flow into the first chamber 11. Therefore, when only the measurement sensor 30 is installed, it is not possible to determine whether the electrical signal of the measurement sensor 30 is caused by acetone or a gas of another component included in the ambient air. Since the reference sensor 40 is disposed in the second chamber 12 into which the ambient air is introduced, the cause of the electrical signal generated from the measurement sensor 30 can be determined by comparing the electrical signal generated from the reference sensor 40 with the electrical signal generated from the measurement sensor 30. For example, if a large electrical signal is generated in the measurement sensor 30 and no electrical signal is generated in the reference sensor 40, the electrical signal of the measurement sensor 30 may be regarded as a signal caused by acetone. However, if a large electric signal is generated in the reference sensor 40, it is difficult to determine whether the electric signal generated in the measurement sensor 30 is caused by the ambient air partially introduced into the first chamber 11 or caused by acetone. In this case, the electrical signal generated from the measurement sensor 30 may be ignored.

In the first chamber 11, there may be formed a guide passage 17 that guides the gas 3 passing through the opening 13 toward the measurement sensor 30. The guide passage 17 connects the surface of the printed circuit board 14 on which the measurement sensor 30 is provided and the inner surface of the first chamber 11 on which the opening 13 is formed. The inner surface of the guide passage 17 surrounds the measurement sensor 30. The inner surface of the guide passage 17 may be inclined so that the guide passage 17 can be widened from the surface on which the opening 13 is formed toward the printed circuit board 14.

In addition, a close contact member 18 surrounding the opening 13 may be provided on the bottom surface of the wall facing the user's skin 1 on which the opening 13 of the first chamber 11 is formed. The contact member 18 protrudes from the bottom surface toward the user's skin 1. The close contact member 18 serves to seal a gap between the user's skin 1 and the bottom surface of the first chamber 11 so that the gas 3 evaporated from the sweat 2 discharged from the user's skin 1 can be introduced into the first chamber 11 as much as possible.

In addition, the wearable body fat combustion measurement device 100 may further include a temperature sensor 35 and a humidity sensor 36. The temperature sensor 35 and the humidity sensor 36 serve to generate electrical signals according to the temperature and humidity of the first chamber 11. The humidity sensor 36 serves to check whether the sweat 2 is sufficiently evaporated from the user's skin 1. When the humidity inside the first chamber 11 is too low, the electrical signal of the measurement sensor 30 may not be caused by acetone evaporated from the sweat 2. In addition, when the temperature inside the first chamber 11 is too low, the electrical signal of the measurement sensor 30 may be caused by the ambient air.

Although not shown, the wearable body fat combustion measurement device 100 may further include a microprocessor such as a microcomputer or the like, a wired/wireless communication unit such as a Bluetooth module or the like, a memory, a display, other types of sensors than described above such as a biosensor and the like, a speaker, a microphone, a battery, etc. These components may be installed in the first chamber 11, the second chamber 12, or a separate space inside the housing 10. These components may be installed on the printed circuit board 14.

In addition, the wearable body fat combustion measurement device 100 includes a signal processor 50. The signal processor 50 may include the aforementioned microprocessor, a memory, and software stored in the memory.

Figure 2:
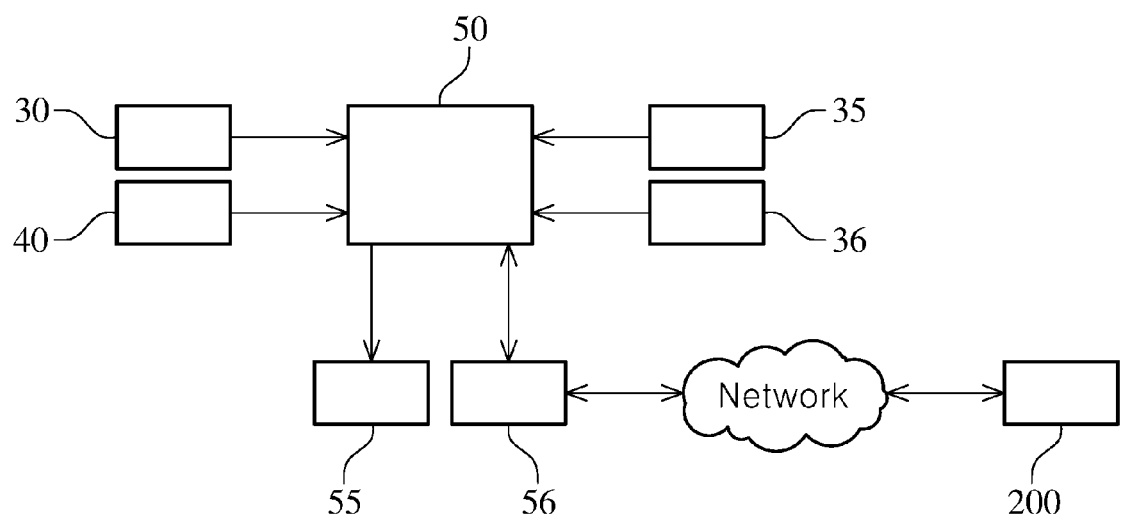
FIG. 2 is a block diagram of the wearable body fat combustion measurement device shown in FIG. 1.

As shown in FIG. 2, the signal processor 50 receives electrical signals from the measurement sensor 30, the reference sensor 40, the temperature sensor 35 and the humidity sensor 36.

The signal processor 50 may calculate an acetone concentration using the electrical signal from the measurement sensor 30, and may calculate a body fat combustion amount using the acetone concentration. The calculated value may be displayed on a display 55 or transmitted to a portable electronic device 200 such as a smartphone or a smart pad through a communication unit 56. In addition, the signal processor 50 calculates a concentration of a gas component contained in the ambient air and detectable by the measurement sensor 30, using the electric signal from the reference sensor 40. When the concentration of the gas component exceeds a predetermined value, the body fat combustion amount calculated by the measurement sensor 30 may be ignored. In addition, the humidity in the first chamber 11 is calculated using the electrical signal from the humidity sensor 36. When the humidity is less than a predetermined value, the body fat combustion amount calculated by the measurement sensor 30 may be ignored. Low humidity indicates that the sweat 2 does not evaporate or that the ambient air has flowed into the first chamber 11. Therefore, it is preferable to ignore the value measured by the measurement sensor 30 at this time. In addition, the temperature in the first chamber 11 is calculated using the electrical signal from the temperature sensor 35. When the temperature is less than a predetermined value, the body fat combustion amount calculated by the measurement sensor 30 may be ignored. Low temperature indicates that the ambient air has flowed into the first chamber 11. Therefore, it is preferable to ignore the value measured by the measuring sensor 30 at this time.

Figure 3:
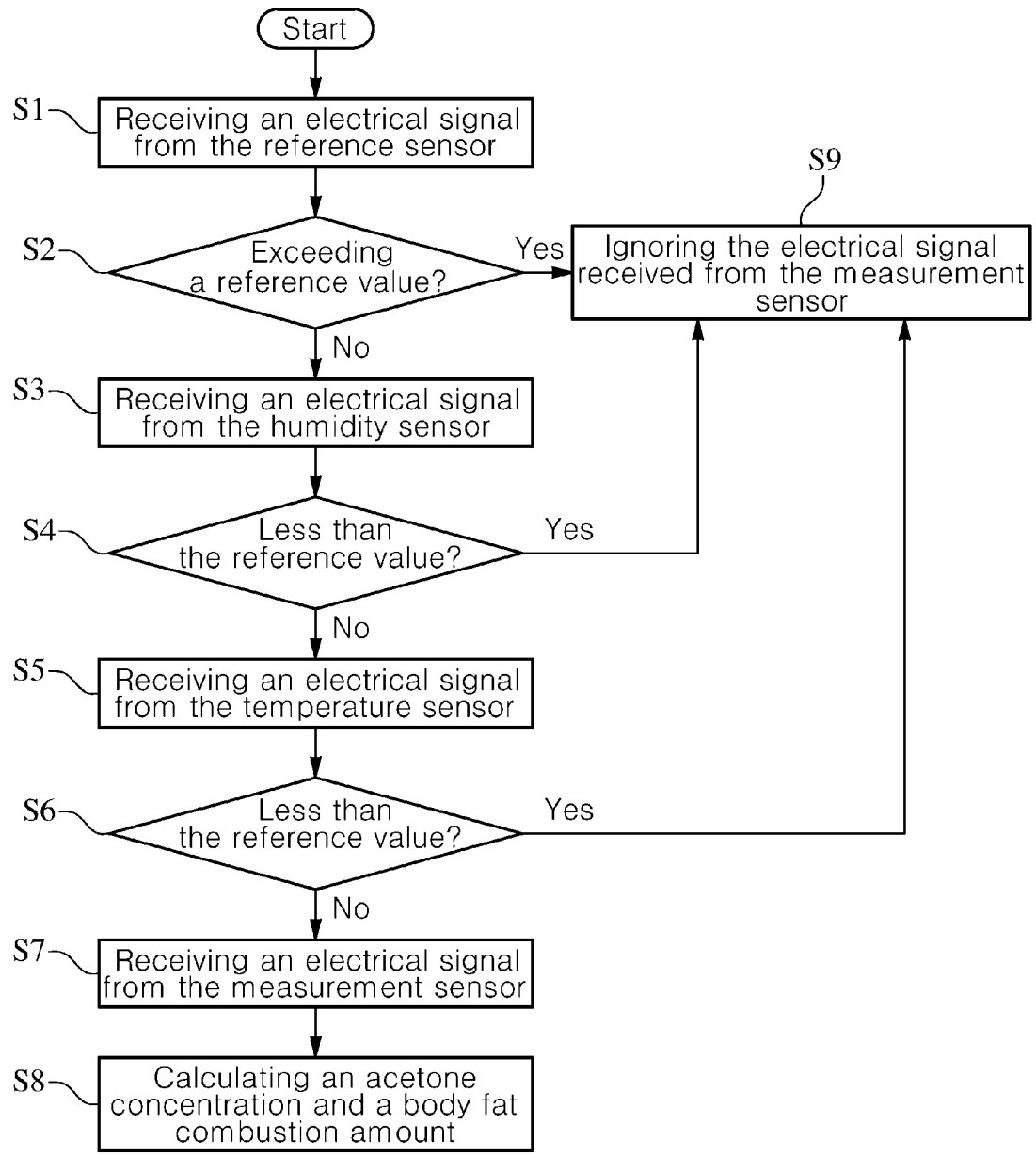
FIG. 3 is a flowchart illustrating an operation of the wearable body fat combustion measurement device shown in FIG. 1.

For example, the signal processor 50 may operate in the order as shown in FIG. 3. First, an electrical signal is received from the reference sensor 35 (S1). It is determined whether the concentration of a gas component, which can be detected by the measurement sensor 30, such as acetone or VOC contained in the ambient air exceeds a reference value (S2). If the concentration of the gas component exceeds the reference value, the electrical signal received from the measurement sensor 30 is ignored (S9). If the concentration of the gas component does not exceed the reference value, an electrical signal is received from the humidity sensor 35 (S3). Then, the humidity in the first chamber 11 is determined using the electric signal (S4). If the humidity in the first chamber 11 is less than a reference value, the electric signal received from the measurement sensor 30 is ignored (S9). Otherwise, an electrical signal is received from the temperature sensor 36 (S5). The temperature in the first chamber 11 is determined using the electrical signal from the temperature sensor 36 (S6). If the temperature in the first chamber 11 is less than a reference value, the electric signal received from the measurement sensor 30 is ignored (S9). Otherwise, an electric signal is received from the measurement sensor 30 (S7). Thus, an acetone concentration and a body fat combustion amount are calculated (S8). The calculated value is displayed on the display 55 or transmitted to the external portable electronic device 200 through the communication unit 56.

The embodiment described above is merely to describe preferred embodiment of the present invention. The scope of the present invention is not limited to the described embodiment. Those skilled in the art may make various changes, modifications or substitutions within the spirit and claims of the present invention. It is to be understood that such changes, modifications or substitutions fall within the scope of the present invention.

What is claimed is:

1. A wearable body fat combustion measurement device, comprising:
    a housing including a first chamber with an opening and a second chamber separated from the first chamber and configured to receive an ambient air;
    a fixing means attached to the housing and configured to bring the housing into contact with a user's skin in a state in which the opening of the first chamber faces the user's skin;
    a measurement sensor disposed inside the first chamber and configured to generate an electrical signal according to an amount of acetone contained in a gas evaporated from sweat discharged from the user's skin and introduced into the first chamber through the opening;
    a reference sensor disposed outside the first chamber and configured to generate an electrical signal according to a concentration of a gas component contained in the ambient air of the second chamber and detectable by the measurement sensor; and
    a signal processor configured to process the electrical signals received from the measurement sensor and the reference sensor,
    wherein the signal processor calculates a concentration of acetone by using the electrical signal received from the measurement sensor, calculates the concentration of the gas component contained in the ambient air and detectable by the measurement sensor by receiving the electrical signal from the reference sensor, and ignores the electrical signal received from the measurement sensor if the concentration of the gas component exceeds a predetermined value, and
    the first chamber is sealed with respect to the second chamber.

2. The device of claim 1, wherein the measurement sensor and the reference sensor are of the same kind.

3. The device of claim 1, wherein
    a printed circuit board configured to seal the first chamber with respect to the second chamber, the measurement sensor provided on one surface of the printed circuit board facing the first chamber, and the reference sensor provided on another surface of the printed circuit board facing the second chamber.

4. The device of claim 3, further comprising:
    a guide passage formed to surround the measurement sensor and configured to connect a surface of the printed circuit board on which the measurement sensor is provided and a surface of the housing on which the opening of the housing is formed, so as to guide the gas passing through the opening to the measurement sensor.

5. The device of claim 1, further comprising:
    a contact member configured to protrude toward the user's skin from a bottom surface of the housing configured to face the user's skin, the contact member configured to surround the opening.

6. The device of claim 1, further comprising:
    a humidity sensor disposed inside the first chamber and configured to generate an electrical signal according to a humidity in the first chamber; and
    wherein the signal processor calculates the humidity in the first chamber by receiving the electrical signal from the humidity sensor, and ignores the electrical signal received from the measurement sensor if the humidity is less than a predetermined value.

7. The device of claim 1, further comprising:
    a temperature sensor disposed inside the first chamber and configured to generate an electrical signal according to a temperature in the first chamber; and
    wherein the signal processor calculates the temperature in the first chamber by receiving the electrical signal from the temperature sensor, and ignores the electrical signal received from the measurement sensor if the temperature is less than a predetermined value.

* * * * *